United States Patent [19]
Caufield et al.

[11] Patent Number: 5,679,801
[45] Date of Patent: Oct. 21, 1997

[54] TETRONIC AND THIOTETRONIC ACID DERIVATIVES AS PHOSPHOLIPASE $A_2$ INHIBITORS

[75] Inventors: Craig E. Caufield, Princeton Junction, N.J.; James M. Rinker, Hamden, Conn.

[73] Assignee: American Home Products Corporation, Madison, N.J.

[21] Appl. No.: 441,500

[22] Filed: May 15, 1995

Related U.S. Application Data

[63] Continuation-in-part of Ser. No. 408,462, Mar. 22, 1995, abandoned, which is a continuation-in-part of Ser. No. 71,415, Jun. 3, 1993, abandoned, which is a division of Ser. No. 685,265, Apr. 12, 1991, Pat. No. 5,242,945.

[51] Int. Cl.$^6$ .................... C07D 307/33; C07D 333/32
[52] U.S. Cl. ................ 549/61; 549/65; 549/313; 549/314; 549/316; 549/317
[58] Field of Search ................ 549/64, 65, 313, 549/314, 316, 317

[56] References Cited

FOREIGN PATENT DOCUMENTS 511633  1/1976  Japan ..................... 549/318

*Primary Examiner*—Robert Gerstl
*Attorney, Agent, or Firm*—Steven R. Eck

[57] ABSTRACT

There are disclosed compounds of the formula:

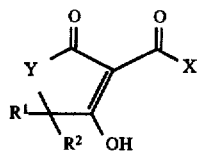

wherein

X is —$CH_2R$;

Y is —O— or —S—;

$R^1$ and $R^2$ are each, independently, hydrogen or lower alkyl;

or a pharmaceutically acceptable salt thereof;

which by virtue of their ability to inhibit $PLA_2$, are of use as antiinflammatory agents and there is also disclosed a method for the treatment of immunoinflammatory conditions, such as allergy, anaphylaxis, asthma and inflammation in mammals.

19 Claims, No Drawings

TETRONIC AND THIOTETRONIC ACID DERIVATIVES AS PHOSPHOLIPASE A₂ INHIBITORS

This application is a continuation-in-part of application Ser. No. 08/408,462, filed Mar. 22, 1995, now abandoned, which is a continuation-in-part of Ser. No. 08/071,415, filed Jun. 3, 1993, now abandoned, which is a division of Ser. No. 07/685,265, filed Apr. 12, 1991, U.S. Pat. No. 5,242,945.

The present invention is directed to certain tetronic acid derivatives having anti-inflammatory activity and to a method for using them as anti-inflammatory agents.

It is now well-established that arachidonic acid (AA) is metabolized in mammals by two distinct pathways. The metabolism of arachidonic acid by cyclooxygenase enzymes results in the production of prostaglandins and thromboxanes. The physiological activity of the prostaglandins has already been amply elucidated in recent years. It is now known that prostaglandins arise from the endoperoxides $PGG_2$ and $PGH_2$ by the cyclooxygenase pathway of arachidonic acid metabolism. These endoperoxides are also the precursors of the thromboxanes (Tx) $A_2$ and $B_2$. $TxA_2$ is a vasoconstrictor which stimulates platelet aggregation. In the normal situation, the vasoconstrictive and platelet aggregating properties of the thromboxanes are balanced by another product arising from the endoperoxides in the cyclooxygenase pathway, prostacyclin ($PGI_2$), which is a vasodilator with platelet aggregation inhibitory activity. In the event prostacyclin synthesis is impaired and/or platelet activation is enhanced, then thrombosis and vasoconstriction is favored. The role of prostanoids in haemostasis and thrombosis are reviewed by R. J. Gryglewski, CRC Crit. Rev. Biochem., 7, 291 (1980) and J. B. Smith, Am. J. Pathol., 99, 743 (1980). Cyclooxygenase metabolites are known to participate directly in the inflammatory response [see Higgs et al., Annals of Clinical Research, 16, 287–299 (1984)]. This is through their vaso-depressor activities, participation in pain and fever and augmentation of peptide mediator vascular permeability and edema forming properties. Finally, various aspects of cell mediated immunity are influenced by cyclooxygenase products.

The other pathway of AA metabolism involves lipoxygenase enzymes and results in the production of a number of oxidative products called leukotrienes. The latter are designated by the LT nomenclature system, and the most significant products of the lipoxygenase metabolic pathway are the leukotrienes $B_4$, $C_4$ and $D_4$. The substance denominated slow-reacting substance of anaphylaxis (SRS-A) has been shown to consist of a mixture of leukotrienes, with $LTC_4$ and $LTD_4$ as the primary products and having varying amounts of other leukotriene metabolites [see Bach et al., J. Immun., 215, 115–118 (1980); Biochem. Biophys. Res. Commun., 93, 1121–1126 (1980)].

The significance of these leukotrienes is that a great deal of evidence is accumulating showing that leukotrienes participate in inflammatory reactions, exhibit chemotactic activities, stimulate lysosomal enzyme release and act as important factors in the immediate hypersensitivity reaction. It has been shown that $LTC_4$ and $LTD_4$ are potent bronchoconstrictors of the human bronchi [see Dahlen et al., Nature, 288,484–486 (1980)], and another leukotriene, $LTB_4$, is a powerful chemotactic factor for leukocytes [see A. W. Ford-Hutchinson, J. Roy. Soc. Med., 74, 831–833 (1981)]. The activity of leukotrienes and slow-reacting substances as mediators of inflammation and hypersensitivity is extensively reviewed in Bailey and Casey, Ann. Reports Med. Chem., 17, 203–217 (1982).

Phospholipase $A_2$ ($PLA_2$) is the critical rate limiting enzyme in the arachidonic acid (AA) cascade since it is responsible for the hydrolysis of esterified AA from the C-2 position of membrane phospholipids. This reaction generates two products (1) free AA which is then available for subsequent metabolism by either the cyclooxygenase or lipoxygenase enzymes and (2) lysophospholipid. When alkylarachidonoyl-glycerophosphatidylcholine is acted upon by the $PLA_2$, the generation of platelet activating factor (PAF) is initiated; PAF is pro-inflammatory in its own right [see Wedmore et al., Br. J. Pharmacol., 74, 916–917 (1981)]. In this regard it may be noted that the anti-inflammatory steroids are thought to inhibit eicosanoid synthesis by inducing the synthesis of a $PLA_2$ inhibitory protein denominated macrocortin or lipomodulin [see Flower et al., Nature, London, 278,456 (1979) and Hirata et al., Proc. Natn. Acad. Sci., U.S.A., 77, 2533 (1980)].

As the initial step leading to subsequent conversion of AA to the various eicosanoids by the cyclooxygenase and lipoxygenase pathways, the $PLA_2$-mediated release of AA from membrane phospholipids is a critical event in attempting to deal with the various physiological manifestations which are based on the activity of the eicosanoids and/or PAF. Thus, while $PLA_2$ has been shown to be required for platelet aggregation [Pickett et al., Biochem. J., 160, 405 (1976)], cardiac contraction and excitation [Geisler et al., Pharm. Res. Commun., 9, 117 (1977)], as well as prostaglandin synthesis [Vogt, Adv. Protagl. Throm. Res., 3, 89 (1978)], the inhibition of $PLA_2$ is indicated in the therapeutic treatment of both PAF induced or cyclooxygenase and/or lipoxygenase pathway product-mediated physiological conditions. Thus, $PLA_2$ inhibitors are a rational approach to the prevention, removal or amelioration of such conditions as allergy, anaphylaxis, asthma and inflammation.

The invention provides novel compound of the formula

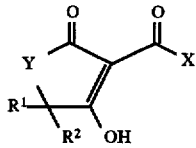

wherein

X is —$CH_2R$;

R is

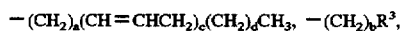

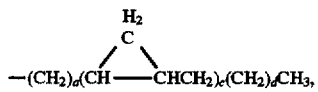

—$(CH_2)_a(C \equiv CCH_2)_c(CH_2)_d CH_3$,

—$(CH_2)_b OR^3$, —$(CH_2)_b SR^3$, —$(CH_2)_b NHR^3$,

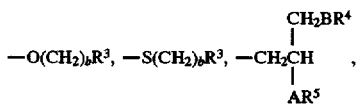

further when Y=S, R may also be —$(CH_2)_e CH_3$;

Y is —O— or —S—;

$R^1$ and $R^2$ are each, independently, hydrogen or lower alkyl;

$R^3$ is indolyl, furyl, phenyl or phenyl optionally mono- or disubstituted independently by alkyl of 1–7 carbon atoms, —C(CH$_3$)$_3$, —C(CH$_3$)$_2$CH$_2$C(CH$_3$)$_3$, —C(CH$_3$)$_2$CH$_2$CH$_3$, haloloweralkyl, perfluoroalkyl, lower alkoxy, aryl alkoxy, halo or nitro;

with the proviso that, when R is —(CH$_2$)$_b$R$^3$, R$^3$ is not furyl;

$R^4$ and $R^5$ are, independently, —COCH$_2$R$^7$, —CO$_2$R$^7$, —CONHR$^7$, geranyl or CH$_2$R$^3$;

$R^6$ is hydrogen or lower alkyl;

$R^7$ is geranyl and any moiety selected from R other than

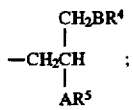

A and B are, independently, —O—, —S— or —NR$^6$—; and a is 0–8;

b is 4–10;

c is 1–3;

d is 0–9; and e is 3–18;

or a pharmaceutically acceptable salt thereof.

A preferred group of compounds of this invention have the structure:

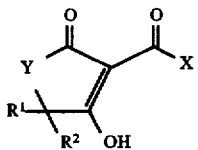

wherein

X is —CH$_2$R;

R is

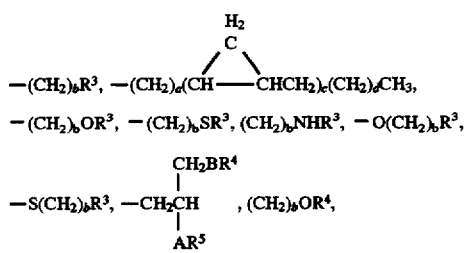

and further when Y=S, R may also be —(CH$_2$)$_e$CH$_3$]; and Y, R$^1$ and R$^2$, R$^3$, R$^4$ and R$^5$, R$^6$, R$^7$, A, a, b, c, d and e are as described above.

The invention further provides a method for treating immunoinflammatory conditions such as allergy, anaphylaxis, asthma and inflammation, in mammals, which comprises administering to a mammal so afflicted an effective amount of a compound having the formula

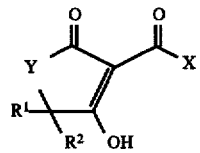

wherein

Y is —O— or —S—;

X is —(CH$_2$)$_a$CH$_3$, —(CH$_2$)$_b$Z or —(CH=CH)$_b$Z when Y=O, and —(CH$_2$)$_a$CH$_3$ when Y=S;

$R^1$ and $R^2$ are each, independently, hydrogen or lower alkyl;

Z is indolyl, furyl, phenyl or phenyl optionally mono- or disubstituted independently by alkyl of 1–7 carbon atoms, haloloweralkyl, perfluoroalkyl, loweralkoxy, aralkoxy, halo or nitro;

with the proviso that when X is —(CH$_2$)$_b$Z, Z is not furyl;

a is 0–20 when Y=O, and a is 1–3 when Y=S; and b is 1–2;

or a pharmaceutically acceptable salt thereof.

The terms "lower alkyl" and "lower alkoxy" refer to moieties having 1 to 6 carbon atoms. The term "aryl" refers to aromatic moieties having 6 to 10 carbon atoms. The term "halo" refers to fluoro, bromo or chloro.

The compounds within the scope of the invention by virtue of their configuration, exhibit stereoisomerism. Accordingly, the compounds of the invention include the diastereomers, enantiomorphs, racemates and mixtures thereof.

The compounds within the scope of the invention can be prepared by a variety of synthetic routes using conventional methods. According to one preparative scheme, a suitable R-containing reactant is condensed with tetronic acid to give an acyl tetronic acid, as exemplified by the condensation of oleic acid and tetronic acid:

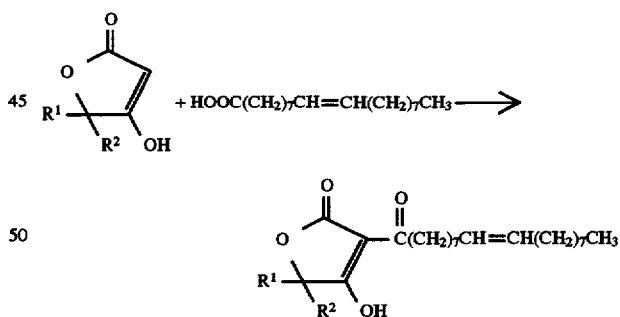

Those compounds of the invention in which R is a moiety of the formula

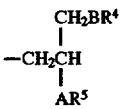

can be prepared by the following procedure. 1-Penten-5-ol is silylated with a suitable silylating agent to yield an intermediate silyloxy diol, which is osmylated to yield a saturated vicinial dihydroxysilyl ether:

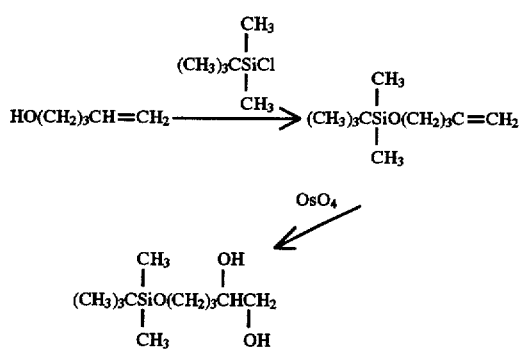

The latter ether can then be condensed, for example, with a suitable alkyl halide in the presence of sodium hydride to yield mono- or bis alkylated intermediates:

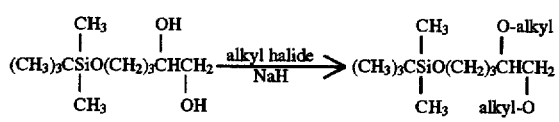

Alternatively, condensation with a carboxylic acid gives a diacylated intermediate, while with an isocyanate, gives a dicarbamoylated intermediate:

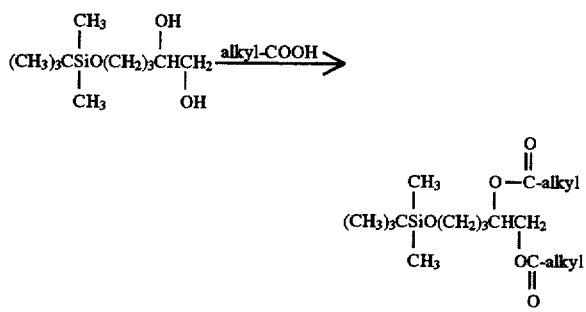

In either case, the resulting intermediate is subjected to deprotection and oxidation to yield, as a reactant, a carboxylic acid, which can then be condensed with tetronic acid to yield the desired final products:

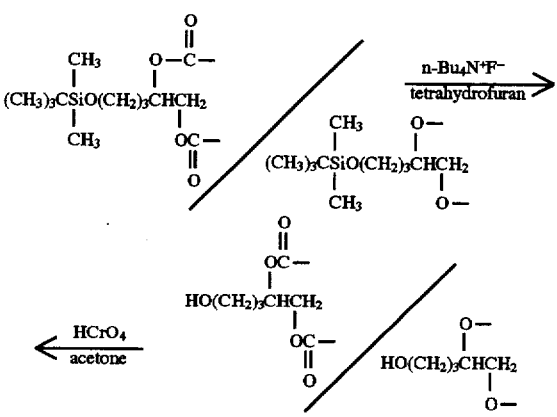

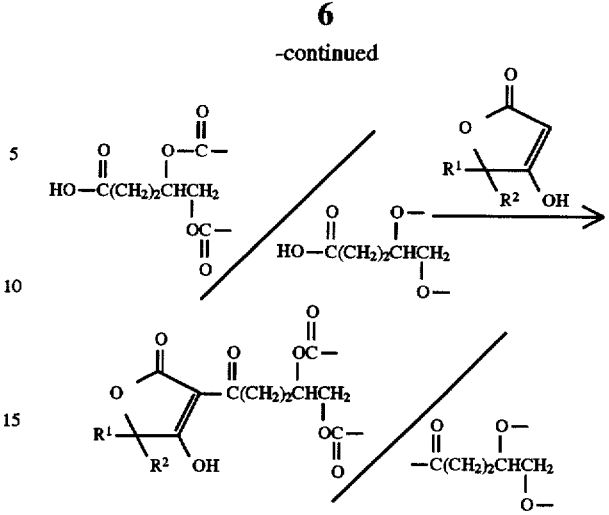

The starting materials in the above preparative sequences are all commercially available or can be prepared by conventional methods as taught in the chemical literature.

The compounds of the invention, by virtue of their ability to inhibit activity of $PLA_2$ enzyme, are useful in the treatment of conditions mediated by products of the oxidation of arachidonic acid. Accordingly, the compounds are indicated in the prevention and treatment of such conditions as allergic rhinitis, allergic bronchial asthma and other naso-bronchial obstructive air-passageway conditions, other immediate hypersensitivity reactions, such as allergic conjunctivitis; and various inflammatory conditions such as those present in rheumatoid arthritis, osteoarthritis, tendinitis, bursitis, psoriasis (and related skin inflammation) and the like.

When the compounds within the scope of the invention are employed in the treatment of allergic airways disorders or in anti-inflammatory therapy, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethyl-cellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally, in which case they are used in the form of a sterile solution containing other solutes, for example, enough saline or glucose to make the solution isotonic. For administration by inhalation or insufflation, the compounds may be formulated into an aqueous or partially aqueous solution, which can then be utilized in the form of an aerosol. The compounds may also be used topically and for this purpose they may be formulated in the form of dusting powders, creams or lotions in pharmaceutically acceptable vehicles, which are applied to affected portions of the skin.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single unit dose, or if desired, the dosage may be divided into convenient subunits administered at suitable times throughout the day.

The standard pharmacological procedures, which are described fully in the examples given hereafter, inter alia, determine the specificity of action of the compounds of the invention as $PLA_2$ inhibitors as measured by their ability to inhibit the synthesis of $LTB_4$ and $TxB_2$ by rat glycogen-elicited polymorphonuclear leukocytes; their ability to inhibit platelet-activating factor and $LTB_4$ biosynthesis in human neutrophils; as well as measure their ability to inhibit arachidonic acid release mediated by human and non-human source $PLA_2$. The procedures further measure the ability of the compounds of the invention to inhibit, in vivo, the activity of exogenously administered $PLA_2$. The pharmacological testing additionally demonstrates the ability of the compounds of the invention to inhibit, in vivo, the lipoxygenase and cyclooxygenase pathways of arachidonic acid metabolism; and also measures the in vivo activity of the compounds as anti-inflammatory agents in the rat carrageenan paw edema assay and the murine ear edema assay.

The following examples show the preparation and pharmacological testing of compounds within the invention.

EXAMPLE 1

4-Hydroxy-3[4-(1H-indol-3-yl)-1oxobutyl]-2-(5H)-furanone

To a solution of 775 mg (7.75 mmol) of tetronic acid in 30 mL of dry dichloromethane is added at 0° C., 1.16 mL (8.53 mmol) of triethylamine and 310 mg (2.58 mmol) of 4-dimethylaminopyridine. After stirring for 5 minutes, 1.89 g (9.3 mmol) of 4-(1H-indol-3-yl)butyric acid is added followed by 1.78 g (9.3 mmol) of 1-(3-dimethylaminopropyl)-3-ethylcarbodiimide hydrochloride. After 10 minutes, the ice bath is removed. The reaction mixture is stirred at room temperature overnight. The reaction mixture is poured into 1.0N HCl and extracted three times with ethyl acetate. The organic layers are combined, washed with brine, dried over anhydrous sodium sulfate, decanted, and concentrated in vacuo to give a brown solid. Trituration with ether gives 1.51 g (68%) of product, m.p 133–135° C.

Spectral data follows. $^1$H NMR (400 MHz, d6-acetone) δ 9.90 (bs, 1H, NH), 7.52 (d, 1H, J=7.3 Hz, arom), 7.32 (d, 1H, J=7.3 Hz, arom), 7.10 (s, 1H, arom), 6.95 (t, 1H, J=7.3 Hz, arom), 6.93 ( t, 1H, J=7.3 Hz, arom), 4.55 (bs, 2H, $CH_2OC=O$), 2.95 (t, 2H, J=6.5 Hz, $CH_2C=O$), 2.85 (t, 2H, J=6.5 Hz, $CH_2Ar$), 2.08 (m, 2H, $CH_2$); IR (KBr) 1760 (C=O) cm$^{-1}$; MS (EI) 285 (M+), 130.

Analysis Calc'd. for $C_{16}H_{15}NO_4 \cdot 0.25H_2O$: C, 66.32; H, 5.35; N, 4.84 Found: C, 66.71; H, 5.73; N, 6.10.

EXAMPLE 2

4-Hydroxy-3[6-(4-chlorophenoxy)-1-oxohexyl]-2-(5H)-furanone

To a stirring solution of 554 mg (5.54 mmol) of tetronic acid in 20 mL of dimethylformamide is added 850 µL (6.09 mmol) of triethylamine and 220 mg (1.765 mmol) of 4-dimethylaminopyridine at 0° C. Next, 1.26 g (6.63 mmol) of 1-(3-dimethylaminopropyl)-3-ethylcarbodiimide hydrochloride and 1.475 g (6.63 mmol) of 6-[4-(hexyloxy) phenoxy]hexanoic acid are added and the reaction mixture is stirred 2 days at room temperature. The reaction is acidified with 1.0N HCl and extracted three times with ether. The combined organic layers are dried over $MgSO_4$ and concentrated in vacuo giving a yellow solid. Pure material is obtained by trituration in ether, filtering to give 774 mg (43%) of 4-hydroxy-3-[6-(4-chlorophenoxy)-1-oxohexyl]-2 (5H)-furanone.

Spectral data follows: $^1$H NMR (CDCl$_3$,400 MHz) 7.216 (d, 2H, Ar), 6.818 (d, 2H, Ar), 4.681 (s, 2H, $CH_2OC=O$), 3.930 (t, 2H, $CH_2OAr$), 2.954 (t, 2H, $O=CCH_2$), 1.836–1.559 (m, 6H, $CH_2$); IR (KBr) 3200, 2980, 2920, 2860, 1775, 1750, 1660, 1620, 1490, 1245, 1050 cm$^{-1}$; MS (EI) 324 (M+), 197, 142, 128 (100), 127.

Analysis Calc'd. for $C_{16}H_{17}O_5Cl \cdot 0.25H_2O$: C, 58.36; H, 5.36

Found: C, 58.78; H, 5.20.

EXAMPLE 3

4-Hydroxy-3-[1-oxo-8-[2-[(2-pentylcyclopropyl) methyl]-cyclopropyl]octyl]-2(5H)-furanone To a stirring solution of 947 mg (9.5 mmol) of tetronic acid in 30 mL of dimethylformamide is added 1.42 mL (10.45 mmol) of triethylamine and 379 mg (3.14 mmol) of 4-dimethylaminopyridine at 0° C. Next, 2.17 g (11.4 mmol) of 1-(3-dimethylaminopropyl)-3-ethylcarbodiimide hydrochloride and 3.5 g (11.4 mmol) of (cis)-7-(2-octylcyclopropyl)octanoic acid are added and the reaction mixture is stirred 2 days at room temperature. The reaction is acidified with 1.0N HCl and extracted three times with ethyl acetate. The combined organic layers are dried over $Na_2SO_4$ and concentrated in vacuo giving a yellow oil. Pure material is obtained by flash chromatography on a 40 mm×150 mm silica column eluting with 50% ethyl acetate/hexane to 100% ethyl acetate giving 870 mg (20%) of 4-hydroxy-3-[1-oxo-8-[2-[(2-pentylcyclopropyl)methyl] cyclopropyl]octyl]-2(5H)-furanone as an oil.

Spectral data follows: $^1$H NMR (CDCl$_3$,400 MHz) δ 4.572 (s, 2H, $CH_2OC=O$), 2.704 (t, 2H, $O=CCH_2$), 1.481 (m, 2H, $O=CCH_2CH_2$), 1.341–1.111 (m, 20H, $CH_2$), 0.845 (t, 3H, $CH_2CH_3$), 0.747–0.644 (m, 4H, cyclopropyl), 0.559 (m, 2H, cyclopropyl), −0.332 (m, 2H, cyclopropyl); IR (KBr) 3060, 2990, 2910, 2840, 1770, 1695, 1655, 1600, 1455, 1435, 1195, 1040 cm$^{-1}$; MS (EI) 390 (M+), 127 (100), 67(94).

Analysis Calc'd. for $C_{24}H_{38}O_4$: C, 73.81; H, 9.81

Found: C, 73.59; H, 9.83.

EXAMPLE 4

(Z)-9-Octadecanoic acid 5-(2,5-dihydro-4-hydroxy-3-furanyl)D-5-oxo-1,2-pentanediyl ester A. 4,5-Bis[((Z)-1-oxo-9-octadecenyl)oxy]pentanoic acid To a stirring solution of 3.76 g (16.1 mmol) of (Z)-5-[[(1,1-dimethyl-ethyl)dimethylsilyl]oxy]-1-pentene-1,2-diol in 50 mL of methylene chloride is added 4.9 mL (35.2 mmol) of triethylamine and 1.3 g of 4-dimethylaminopyridine at 0° C. Next, 7.4 g (38.6 mmol) of 1-(3-dimethylaminopropyl)-3-ethylcarbodiimide hydrochloride and 10 g (35.4 mmol) of oleic acid are added and the reaction mixture is stirred overnight at room temperature. The reaction is poured into water and extracted with four 50 mL portions of methylene chloride. The combined organic layers are dried over $MgSO_4$ and concentrated in vacuo. The resulting crude diester dissolved in 32 mL of tetrahydrofuran and treated with 32 mL (32 mmol) of 1.0N tetrabutyl-ammonium fluoride in tetrahydrofuran and the reaction is stirred 2 hours at room temperature. The reaction is poured into water and extracted with four 50 mL portions of ether. The combined organic layers are dried over $MgSO_4$ and concentrated in vacuo affording crude compound. Pure material was obtained by flash chromatography with 15% ethyl acetate/hexane as eluant giving 7.7 g (77%) of alcohol. Next, 20 mL of 2.0M Jones reagent is added at 0° C. to a stirring solution of 7.7 g (11.86 mmol) of the alcohol and the reaction is stirred for 2 hours. The reaction is poured into water and extracted with four 50 ml portions of ether. The combined organic layers are dried over $MgSO_4$ and concentrated in vacuo affording crude compound. Pure material was obtained by flash chromatography with 35% ethyl acetate/hexane as eluant giving 2.2 g (28%) of 4,5-bis[((Z)-1-oxo-9-octadecyl)oxy]pentanoic acid.

Spectral data follows: $^1H$ NMR ($CDCl_3$, 400 MHz) δ 5.344 (m, 4H, HC=CH), 5.175 (m, 1H, HCOC=O), 4.145 (m, 2H, $H_2COC$=O), 2.422 (t, 2H, $HO_2CCH_2$), 2.301 (t, 4H, O(C=O)$CH_2$), 2.012 (m, 8H, C=$CCH_2$), 1.612 (m, 4H, O(C=O)$CH_2CH_2$), 1.289 (m, 40H, $CH_2$), 0.881 (t, 6H, $CH_2CH_3$); IR (KBr) 3000, 2920, 2840, 1740,1710,1460, 1160 $cm^{-1}$; MS ($CI^+$) 664 ($MH^{++}$), 663 ($MH^+$), 645, 381 (100), 338, 265, 159, 87.

Analysis Calc'd. for $C_{41}H_{74}O_6$: C, 74.27; H, 11.25 Found: C, 73.92; H, 11.28.

B) (Z)-9-Octadecanoic acid 5-(2,5-dihydro-4-hydroxy-3-furanyl)-5-oxo- 1,2-pentanediyl ester To a stirring solution of 137 mg (1.37 mmol) of tetronic acid in 10 mL of dimethylformamide are added 220 μL (1.5 mmol) of triethylamine and 70 mg of 4-dimethylaminopyridine at 0° C. Next, 330 mg (1.72 mmol) of 1-(3-dimethylaminopropyl)-3-ethylcarbodiimide hydrochloride and 1.0 g (1.5 mmol) of 4,5-bis[((Z)-1-oxo-9-octadecenyl)oxy]pentanoic acid and the reaction is stirred overnight at room temperature. The reaction is acidified with 1.0N HCl and extracted with four 50 mL portions of ether. The combined organic layers are dried over $MgSO_4$ and concentrated in vacuo affording crude compound. Pure material was obtained by flash chromatography with 10% methanol/ethyl acetate as eluant affording 608 mg (60) of (Z)-9-octadecanoic acid 5-(2,5-dihydro-4-hydroxy-3-furanyl)-5-oxo-1,2-pentanediyl ester.

Spectral data follows: $^1H$ NMR ($d_6$-DMSO, 400 MHz) δ 6.68 (bs, 1H, OH), 5.290 (m, 4H, HC=CH), 4.980 (s, 1H, HCOC=O), 4.500 (s, 2H, $CH_2OC$=O), 4.216 (s, 1H, $CH_2OC$=O), 3.974 (s, 1H, $CH_2OC$=O), 2.726 (m, 2H, O=$CCH_2$), 2.218 (s, 4H, O=$CCH_2$), 1.953 (m, 8H, C=$CCH_2$), 1.477 (s, 4H, O=$CCH_2CH_2$), 1.220 (s, 40H, $CH_2$), 0.830 (t, 6H, $CH_2CH_3$); IR (KBr) 3000, 2900, 2840, 1760,1730, 1690, 1650, 1600, 1460, 1450, 1430, 1220, 1165, 1035, 1010 $cm^{-1}$; MS ($CI^+$) 463, 409 (100), 265, 69.

Analysis Calc'd. for $C_{45}H_{76}O_8$: C, 72.54; H, 10.28 Found: C, 72.58; H, 10.48.

EXAMPLE 5

3[9-(4-Chlorophenoxy)]-1-oxononyl]-4-hydroxy-2 (5H)-furanone

To a stirring solution of 736 mg (7.36 mmol) of tetronic acid in 30 mL of dimethylformamide is added 1.2 mL (8.09 mmol) of triethylamine and 300 mg of 4-dimethylaminopyridine at 0° C. Next, 1.7 g (8.86 mmol) of 1-(3-dimethylaminopropyl)-3-ethylcarbodiimide hydrochloride and 2.6 g (8.06 mmol) of 9-(4-chlorophenoxy) nonanoic acid are added and the reaction is stirred overnight at room temperature. The reaction is acidified with 1.0N HCl and extracted with four 50 mL portions of ether. The combined organic layers are dried over $MgSO_4$ and concentrated in vacuo affording crude compound. Pure material is obtained by flash chromatography with 10% methanol/ethyl acetate as eluant affording 800 mg (30%) of 3-[9-(4-chlorophenoxy)-1-oxononyl]-4-hydroxy-2(5H)-furanone.

Spectral data follows: $^1H$ NMR ($CDCl_3$, 400 MHz) δ 7.216 (d, 2H, Ar), 6.813 (d, 2H, Ar), 4.614 (s, 2H, $CH_2OC$=O), 3.911 (t, 2H, $OCH_2Ar$), 2.912 (t,2H, O=$CCH_2$), 1.742 (m, 4H, $CH_2$), 1.370 (m, 8H, $CH_2$); IR (KBr) 3220, 2940, 2860, 1770, 1745, 1660, 1610, 1600, 1495, 1475, 1435, 1395, 1345, 1290, 1270, 1250, 1210, 1175, 1130, 1110, 1100, 1060, 1010, 825 $cm^{-1}$; MS ($CI^+$) 367 ($MH^+$), 277, 275 (100), 257, 239, 91, 61.

Analysis Calc'd for $C_{19}H_{23}ClO_5$: C, 62.21; H, 6.32 Found: C, 61.82; H, 6.25.

EXAMPLE 6

Hexylcarbamic acid 5-(2,5-dihydro-4-hydroxy-2-oxo-3-furanyl)-5-oxo-1,2-pentanediyl ester To a stirring solution of 234 mg (2.34mmol) of tetronic acid in 20 mL of dimethylformamide is added 400 μL (2.57 mmol) of triethylamine and 200 mg of 4-dimethylaminopyridine at 0° C. Next, 600 mg (3.12 mmol) of 1-(3-dimethylaminopropyl)-3-ethylcarbodiimide and 1.0 g (2.57 mmol) of 4,5-bis[[(hexylamino)carbonyl]-oxy]pentanoic acid are added and the reaction is stirred 3 days at room temperature. The reaction is acidified with 1.0N HCl and extracted with three 100 mL portions of ether. The combined organic layers are dried over $MgSO_4$ and concentrated in vacuo affording 636 mg (58%) of hexylcarbamic acid 5-(2,5-dihydro-4-hydroxy-2-oxo-3-furanyl)-5-oxo-1,2-pentanediyl ester.

Spectral data follows: $^1H$ NMR ($CDCl_3$, 400 MHz) δ 4.896 (m, 1H, HCOC=O), 4.792 (m, 2H, NH), 4.628 (s, 2H, $CH_2OC$=O), 4.157 (m, 2H, $H_2COC$=O), 3.152 (m, 6H, $NHCH_2$, O=$CCH_2$), 2.047 (m, 2H, O=$CCH_2CH_2$), 1.485 (m, 4H, $HNCH_2CH_2$), 1.289 (m, 12H, $CH_2$), 0.885 (t, 6H, $CH_2CH_3$); IR (KBr) 3350, 2960, 2935, 2860, 1750, 1700, 1645, 1580, 1550, 1465,1275, 1040 $cm^{-1}$; MS (pos.ion FAB) 515 ($MNa^{++}$), 493 ($MNa^+$), 370, 350, 181, 102, 55, 43 (100).

Analysis Calc'd. for $C_{23}H_{38}N_2O_8$: C, 58.71; H, 8.14; N, 5.95 Found: C, 58.77; H, 8.19; N, 5.77

EXAMPLE 7

Dodecylcarbamic acid 5-(2,5-dihydro-4-hydroxy-2-oxo-3-furanyl)-5-oxo-1,2-pentanediyl ester A) 4,5-Bis[[(Dodecylamino)carbonyl]oxy]pentanoic acid To a stirring solution 1.9 g (9.47 mmol) of 1.9 g (9.47 mmol) of the (Z)-5-[[(1,1-dimethylethyl)dimethylsilyl]oxy]-1-pentene-1,2-diol in 20 mL of methylene chloride is added 3.2 mL (23 mmol) of triethylamine and 4.8 g (9.47 mmol) of dodecyl isocyanate at 0° C. and the reaction is stirred for 2 days at room temperature. The reaction is diluted with methylene chloride and washed with 1.0N HCl, saturated sodium bicarbonate, and brine, dried over sodium sulfate and concentrated in vacuo. The resulting dicarbamate is dissolved in 20 mL of tetrahydrofuran and treated with 20 mL of 1.0M tetrabutylammonium fluoride in tetrahydrofuran and the reaction is stirred overnight at room temperature. The reaction mixture was poured into water and extracted with three 100 mL portions of ether. The combined organic layers are dried over MgSO$_4$ and concentrated in vacuo affording crude compound. Pure material is obtained by flash chromatography with ethyl acetate as eluant affording 4.1 g (80%) of alcohol. Next, 12 mL of 2.0M Jones reagent is added at 0° C. to a stirring solution of 4.1 g (7.62 mmol) of the alcohol in 75 mL of acetone and the reaction is stirred for 4 hours. The reaction is poured into water and extracted with three 100 mL portions of ether. The combined organic layers are dried over MgSO$_4$ and concentrated in vacuo, affording 2.1 g (50%) of 4,5-bis[[dodecylamino)carbonyl] oxy]pentanoic acid.

Spectral data follows: $^1$H NMR (CDCl$_3$, 400 MHz) 4.961 (m, 1H, HCOC=O), 4.741 (m, 2H, NH), 4.110 (m, 2H, H$_2$COC=O), 3.130 (m, 4H, HNCH$_2$), 2.425 (m, 2H, HO$_2$CCH$_2$), 1.897 (m, 2H, HO$_2$CCH$_2$CH$_2$), 1.466 (m, 4H, HNCH$_2$CH$_2$), 1.242 (s, 3H, CH$_2$), 0.866 (t, 6H, CH$_2$CH$_3$); IR (KBr) 3450, 2930, 2860, 1700, 1660, 1470, 1280 cm$^{-1}$; MS (pos.ion FAB) 579 (M$^+$Na), 557 (MH$^+$), 328 (100), 230, 186, 117, 91, 73, 57, 43, 30.

Analysis Calc'd. for C$_{31}$H$_{60}$N$_2$O$_6$: C, 66.87; H, 10.86; N, 5.03

Found: C, 67.30; H, 11.06; N, 5.06

B) Dodecylcarbamic acid 5-(2,5-dihydro-4-hydroxy-2-oxo-3-furanyl)-5-oxo-1,2-pentanediyl ester To a stirring solution of 163 mg (1.63 mmol) of tetronic acid in 20 mL of dimethylformamide is added 250 µL ( 1.8 mmol) of triethylamine and 100 mg of 4-dimethylaminopyridine at 0° C. Next, 400 mg (2.08 mmol) of 1-(3-dimethylaminopropyl)-3-ethylcarbodiimide hydrochloride and 1.0 g (1.8 mmol) of 4,5-bis-[[ (dodecylamino)carbonyl]oxy]pentanoic acid are added and the reaction is stirred 3 days at room temperature. The reaction is acidified with 1.0N HCl and extracted with three 100 mL portions of ether. The combined organic layers are dried over MgSO$_4$ and concentrated in vacuo affording crude compound. Pure material is obtained by flash chromatography with 10% methanol/ethyl acetate as eluant affording 500 mg (50%) of dodecylcarbamic acid 5-(2,5-dihydro-4-hydroxy-2-oxo-3-furanyl)-5-oxo-1,2-pentanediyl ester.

Spectral data follows: $^1$H NMR (CDCl$_3$, 400 MHz) δ 4.896 (m, 1H, HCOC=O), 4.792 (m, 2H, NH), 4.628 (s, 2H, CH$_2$OC=O), 4.157 (m, 2H, H$_2$COC=O), 3.152 (m, 6H, O=CCH$_2$, NHCH$_2$), 2.047 (m, 2H, O=CCH$_2$CH$_2$), 1.485 (m, 4H, NHCH$_2$CH$_2$), 1.289 (m, 36H, CH$_2$), 0.885 (t, 6H, CH$_2$CH$_3$); IR (KBr) 3350, 2960, 2935, 2860, 1750, 1700, 1645, 1580, 1550, 1465, 1275, 1040 cm$^{-1}$; MS (pos.ion FAB) 683 (MNa$^{++}$), 661 (MNa$^+$), 237, 221,186,131,91,73, 57 (100).

Analysis Calc'd. for C$_{35}$H$_{62}$N$_2$O$_8$: C, 65.80; H, 9.78; N, 4.38 Found : C, 66.19; H, 9.86; N, 4.26.

EXAMPLE 8

4-Hydroxy-3-[6-[4-[(4-chlorophenyl)methoxyphenoxy]]-1-oxohexyl]2(5H-furanone

To a stirring solution of 757 mg (7.57 mmol) of tetronic acid in 50 mL of dimethylformamide is added 1.20 mL (8.83 mmol) of triethylamine and 400 mg of 4-dimethylaminopyridine at 0° C. Next, 2.00 g (8.3 mmol) of 1-(3-dimethylaminopropyl)-3-ethylcarbodiimide hydrochloride and 2.88 g (8.3 mmol) of 6-[4-(4-chlorophenyl)methoxyphenoxy]hexanoic acid are added and the reaction mixture is stirred 3 days at room temperature. The reaction is acidified with 1.0N HCl and extracted three times with ethyl acetate. The combined organic layers are dried over MgSO$_4$ and concentrated in vacuo giving a yellow oil. Pure material was obtained by flash chromatography on a 40 mm×150 mm silica column eluting with 10% methanol/ ethyl acetate giving 800 mg (25%) of 4-hydroxy-3-[6-[4-[ (4-chlorophenyl)methoxyphenoxy]]-1-oxohexyl]-2(5H)-furanone.

Spectral data follows: $^1$H NMR (CDCl$_3$,400 MHz) 8 7.338 (s, 4H, Ar), 6.849 (d, 2H, Ar), 6.811 (d, 2H, Ar), 4.966 (s, 2H, CH$_2$Ar), 4.611 (s, 2H, CH$_2$OC=O), 3.899 (t, 2H, CH$_2$Ar), 2.964 (t, 2H, O=CCH$_2$), 1.824–1.546 (m, 6 H, CH$_2$); IR (KBr) 3420, 2945, 2860, 1770, 1660, 1615, 1515, 1245, 1030 cm$^{-1}$; MS (EI) 430 (M+), 197, 127, 125 (100).

Analysis Calc'd. for C$_{23}$H$_{25}$O$_6$Cl: C, 64.11; H, 5.38 Found: C, 63.98; H, 5.45.

EXAMPLE 9

4-Hydroxy-3-[6-[4-(hexyloxy)phenoxyl]-1-oxohexyl]-2(5H )-furanone

To a stirring solution of 876 mg (8.76 mmol) of tetronic acid in 50 mL of dimethylformamide is added 1.40 mL (10.30 mmol) of triethylamine and 400 mg of 4-dimethylaminopyridine at 0° C. Next, 2.00 g (8.3 mmol) of 1-(3-dimethylaminopropyl)-3-ethylcarbodiimide hydrochloride and 2.97 g (8.3 mmol) of 6-[4-(hexyloxy)phenoxy] hexanoic acid are added and the reaction mixture is stirred 3 days at room temperature. The reaction is acidified with 1.0N HCl and extracted three times with ethyl acetate. The combined organic layers are dried over MgSO$_4$ and concentrated in vacuo giving a yellow oil. Pure material was obtained by flash chromatography on a 40 mm×150 mm silica column eluting with 10% methanol/ethyl acetate giving 1.1 g (32%) of 4-hydroxy-3-[6-[4-(hexyloxy)phenoxy]-1-oxohexyl]-2(5H)-furanone.

Spectral data follows: $^1$H NMR (CDCl$_3$, 400 MHz) δ 4.601 (s, 2H, CH$_2$OC=O), 3.910 (s, 4H, CH$_2$Ar), 2.951 (t, 2H, O=CCH$_2$), 1.815–1.309 (m, 14 H, CH$_2$), 0.918 (t, 3H, CH$_2$CH$_3$); IR (KBr) 2950, 2880, 1770, 1680, 1650, 1615, 1520, 1250, 1040 cm$^{-1}$; MS (CI) 391 (MH+), 349, 291, 117 (100).

Analysis Calc'd for C$_{22}$H$_{30}$O$_6$: C, 67.67; H, 7.74 Found: C, 67.70; H, 7.70.

EXAMPLE 10

4-Hydroxy-3-[7-(4-chlorophenoxy)-1-oxoheptyl]-2 (5H )-furanone

To a stirring solution of 1.00 g (10 mmol) of tetronic acid in 40 mL of dimethylformamide is added 1.51 mL (11.11 mmol) of triethylamine and 402 mg (3.33 mmol) of 4-dimethylaminopyridine at 0° C. Next, 2.29 g (11.97 mmol) of 1-(3-dimethylaminopropyl)-3-ethylcarbodiimide hydrochloride and 3.07 g (11.97 mmol) of 7-(4-chlorophenoxy)heptanoic acid are added and the reaction mixture is stirred 2 days at room temperature. The reaction is acidified with 1.0N HCl and extracted three times with ethyl acetate. The combined organic layers are dried over Na$_2$SO$_4$ and concentrated in vacuo giving a yellow oil. Pure material was obtained by flash chromatography on a 40 mm×150 mm silica column eluting with 10% methanol/ ethyl acetate giving 1.50 g (44%) of 4-hydroxy-3-[7-(4-chlorophenoxy)-1-oxoheptyl]-2(5H)-furanone.

Spectral data follows: $^1$H NMR (CDCl$_3$,400 MHz) δ 7.290 (d, 2H, Ar), 6.928 (d, 2H, Ar), 4.488 (s, 2H, CH$_2$OC=O), 3.924 (t, 2H, CH$_2$OAr), 2.711 (t, 2H, O=CCH$_2$), 1.694–1.298 (m, 8H,CH$_2$); IR (KBr) 3210, 2960, 2880, 1773, 1760, 1665, 1620, 1500, 1480, 1440, 1355, 1060 cm$^{-1}$; MS (EI) 338 (M+), 211 (100), 193, 128.

Analysis Calc'd. for $C_{17}H_{19}O_5Cl \cdot 0.25H_2O$: C, 59.48; H, 5.69 Found: C, 59.27; H, 5.79.

EXAMPLE 11

3-[6-(4-Heptylphenoxy)-1-oxohexyl]-4-hydroxy-2(5H)-furanone

To a stirring solution of 1.1 g (10.98 mmol) of tetronic acid in 25 mL of dimethylformamide is added 1.53 mL (10.98 mmol) of triethylamine and 400 mg of 4-dimethylaminopyridine at 0° C. Next, 2.28 g (11.98 mmol) of 1-(3-dimethylaminopropyl)-3-ethylcarbodiimide hydrochloride and 3.38 g (10.98 mmol) of 6-(4-heptylphenoxy)heptanoic acid are added and the reaction mixture is stirred for 3 days at room temperature. The reaction mixture is acidified with 1.0N HCl and extracted with three 200 mL portions of ether. The combined organic layers are dried over MgSO$_4$ and concentrated in vacuo. Trituration of the crude product in ethyl acetate/hexane affords 2.1 g (50%) of 3-[6-(4-heptylphenoxy)-1-oxohexyl]-4-hydroxy-2(5H)-furanone.

Spectral data follows: $^1$H NMR (CDCl$_3$, 400 MHz) δ 7.071 (d, 2H, Ar), 6.797 (d, 2H, Ar), 4.608 (s, 2H,CH$_2$OC=O), 3.935 (t, 2H, OCH$_2$), 2.949 (t, 2H, O=CCH$_2$), 2.523 (t, 2H, CH$_2$Ar), 1.786 (m, 4H, O=CCH$_2$CH$_2$), 1.573 (m, 4H, ArCH$_2$CH$_2$), 1.284 (m, 8H, CH$_2$), 0.873 (t, 3H, CH$_2$CH$_3$); IR (KBr) 3450, 3200, 2920, 2850, 1780, 1750, 1660, 1615, 1510, 1460, 1430, 1385, 1340, 1245, 1175, 1125, 1050, 1010, 830 cm$^{-1}$; MS (EI) 388 (M$^+$), 197, 192, 127, 107 (100).

Analysis Calc'd. for $C_{23}H_{32}O_5$: C, 71.10; H, 8.30 Found: C, 71.23; H, 8.36.

EXAMPLE 12

(Z)-9-Octadecanoic acid 4-(2,5-dihydro-4-hydroxy-2-oxo-3-furanyl)-4-oxobutanoic ester (Z)-9-octadecanoic acid 4-hydroxybutyl ester To a stirring solution of 2.0 g (7.0 mmol) of oleic acid and 1.6 g (7.0 mmol) of 2-(4-bromobutoxy)tetrahydro-2H-pyran in 20 mL of tetrahydrofuran is added 2.3 g (7.1 mmol) of cesium carbonate and the reaction mixture is stirred overnight at room temperature. The reaction mixture is poured into water and extracted with three 100 mL portions of ether. The combined organic layers are dried over MgSO$_4$ and concentrated in vacuo affording 2.9 g (100%) of (Z)-9-octadecanoic acid 4-[(tetrahydro-2H-pyran-2-yl)oxy]butyl ester. Next, 500 mg of Dowex 50W 8X resin is added to a stirring solution of 2.9 g (7.0 mmol) of (Z)-9-octadecanoic acid 4-[(tetrahydro-2H-pyran-2-yl)oxy]butyl ester in 100 mL of 1:1 tetrahydrofuran/methanol and the reaction mixture is stirred overnight at room temperature. The reaction mixture is filtered and concentrated in vacuo affording 2.4 g (100%) of alcohol. Next, 11 mL of 2.0M Jones reagent is added at 0° C. to a stirring solution of 2.4 g (7.0 mmol) of alcohol in 75 mL of acetone and the reaction mixture is stirred for 2 hours. The reaction mixture is poured into water and extracted with three 50 mL portions of ether. The combined organic layers are dried over MgSO$_4$ and concentrated in vacuo affording 2.1 g (81%) of title compound.

Spectral data follows: $^1$H NMR (CDCl$_3$, 400 MHz) δ 5.332 (m, 2H, HC=CH), 4.126 (t, 2H, O=COCH$_2$), 2.405 (t, 2H, HO$_2$CCH$_2$), 2.283 (t, 2H, O(C=O)CH$_2$), 2.003 (m, 4H, C=CCH$_2$), 1.595 (m, 2H, O=CCH$_2$CH$_2$), 1.270 (m, 22H, CH$_2$), 0.867 (t, 3H, CH$_2$CH$_3$).

B) (Z)-9-Octadecanoic acid 4-(2,5-dihydro-4-hydroxy-2-oxo-3-furanyl)-4-oxobutanoic ester To a stirring solution of 570 mg (5.7 mmol) of tetronic acid in 50 mL of dimethylformamide is added 795 µL (5.7 mmol) of triethylamine and 400 mg of 4-dimethylaminopyridine at 0° C. Next, 1.2 g (6.26 mmol) of 1-(3-dimethylaminopropyl)-3-ethylcarbodiimide hydrochloride and 2.1 g of (Z)-9-octadecanoic acid 4-hydroxybutyl ester are added and the reaction mixture is stirred overnight at room temperature. The reaction mixture is acidified with 1.0N HCl and extracted with three 100 mL portions of ethyl acetate. The combined organic layers are dried over MgSO$_4$ and concentrated in vacuo affording crude product. Pure material is obtained by flash chromatography with 10% methanol/ethyl acetate as eluant affording 1.8 g (72%) of (Z)-9-octadecanoic acid 4-(2,5-dihydro-4-hydroxy-2-oxo-3-furanyl)-4-oxobutanoic ester.

Spectral data follows: $^1$H NMR (CDCl$_3$, 400 MHz) δ 5.332 (m, 2H, HC=CH), 4.616 (s, 2H, CH$_2$O C=O), 4.126 (t, 2H, O=COCH$_2$), 3.004 (t, 2H, O=CCH$_2$), 2.283 (t, 2H, O(C=O)CH$_2$), 2.003 (m, 4H, C=CCH$_2$), 1.595 (m, 2H, O=CCH$_2$CH$_2$), 1.270 (m, 22H, CH$_2$), 0.867 (t, 3H, CH$_2$CH$_3$); IR (KBr) 3025, 2935, 2865, 1775, 1735, 1705, 1610, 1520, 1470, 1440, 1230, 1180, 1045, 1015 cm$^{-1}$; MS (CI$^+$) 451 (MH$^+$), 297, 283, 265, 183, 169 (100), 102.

Analysis Calc'd. for $C_{26}H_{42}O_6$: C, 69.30; H, 9.39 Found: C, 69.08; H, 9.37.

EXAMPLE 13

4-Hydroxy-3-[6-(1,1,3,3-tetramethylbutyl)phenoxy)-1oxohexyl]-2(5H)-furanone

To a stirring solution of 329 mg (3.29 mmol) of tetronic acid in 15 mL of dimethylformamide is added 458 µL (3.29 mmol) of triethylamine and 220 mg (1.765 mmol) of 4-dimethylaminopyridine at 0° C. Next, 681 mg (3.58 mmol) of 1-(3-dimethylaminopropyl)-3-ethylcarbodiimide hydrochloride and 1.0 g (3.29 mmol) of 6-(1,1,3,3-tetramethylbutyl)phenoxy)hexanoic acid are added and the reaction mixture is stirred overnight at room temperature. The reaction is acidified with 1.0N HCl and extracted three times with ether. The combined organic layers are dried over MgSO$_4$ and concentrated in vacuo giving a yellow solid. Flash chromatography on a 40 mm×150 mm silica gel column eluting with 10% methanol/ethyl acetate gives 650 mg (50%) of 4-hydroxy-3-[6-( 1,1,3,3-tetramethylbutyl)phenoxy)-1-oxohexyl]-2(5H)-furanone.

Spectral data follows: $^1$H NMR (CDCl$_3$,400 MHz) δ 7.255 (d, 2H, Ar), 6.778 (d, 2H, Ar), 4.599 (s, 2H, CH$_2$OC=O), 3.935 (t, CH$_2$OAr), 2.947 (t, 2 H, O=CCH$_2$), 1.824–1.573 (m, 6H, CH$_2$), 1.688 (s, 2H, CH$_2$), 1.330 (3, 6H, C(CH$_3$)$_2$), 0.705 (s, 9H, t-Bu); IR (KBr) 2960, 2870, 1775, 1695, 1655, 1610, 1510, 1250, 1040 cm$^{-1}$; MS (EI) 402 (M+), 331 (100), 127.

Analysis Calc'd. for $C_{24}H_{34}O_5$: C, 71.61; H, 8.51 Found: C, 71.70; H, 8.42.

EXAMPLE 14

((Z)9-octadecynyl)carbamic acid 1-[[((E)-3,7-Dimethyl-2,6-octadecadienyl) oxy]methyl]-4-(2,5-dihydro-4-hydroxy-2-oxo-3-furanyl)-4-oxobutyl ester A) 5[((E)-3,7-Dimethyl-2,6-octadienyl)oxy]-4-[[((Z)-9-octadecenylamino)carbonyl]oxy]pentanoic acid To a stirring suspension of 140 mg (4.6 mmol) of 80% NaH in 5 mL of tetrahydrofuran is added 1.07 g (4.6 mmol)

of (Z)-5-[[(1,1-dimethylethyl)dimethylsilyl]oxy]-1-pentene-1,2-diol at 0° C. and the reaction mixture is stirred for 1 hour. Next, 1.0 g (4.6 mmol) of geranyl bromide is added and the reaction is stirred overnight at room temperature. The reaction mixture is poured into water and extracted with three 50 mL portions of ethyl acetate. The combined organic layers are dried over MgSO$_4$ and concentrated in vacuo affording 1.7 g (100%) of (E)-5-[[(1,1-dimethylethyl)dimethylsilyl]oxy]-1-[(3,7-dimethyl-2,6-octadienyl)oxy]-2-pentanol. Next, 1.6 g (4.3 mmol) of (E)-5-[[( 1,1-dimethylethyl)dimethylsilyl]oxy]-1-[(3,7-dimethyl-2,6-octadienyl)oxy]-2-pentanol and 800 µL (5.73 mmol) of triethylamine in 20 mL of methylene chloride are added at 0° C. to a stirring solution of 13.3 mL of 20% phosgene in toluene and the reaction mixture is stirred for 1 hour. The reaction mixture is concentrated in vacuo and redissolved in 20 mL of tetrahydrofuran. Next, 1.3 g (4.6 mmol) of oleyl amine is added and the reaction mixture is stirred for 2 hours. The reaction mixture is poured into water and extracted with three 50 mL portions of ether. The organic layers are dried over MgSO$_4$ and concentrated in vacuo affording crude product. Pure material is obtained by flash chromatography with 10% ethyl acetate/ hexane as eluant affording 1.67 g (67%) of (Z)-9-octadecenylcarbamic acid (E)-5-[[(1,1-dimethylethyl) dimethylsilyl]oxy]-1-[[(3,7-dimethyl-2,6-octadienyl)oxy]-methyl]butyl ester. Next, 5 mL of 1.0M tetrabutylammonium fluoride in tetrahydrofuran is added to a stirring solution of 1.67 g (2.5 mmol) of (Z)-9-octadecenylcarbamic acid (E)-5-[[(1,1-dimethylethyl) dimethyl]oxy]-1-[[(3,7-dimethyl-2,6-octadienyl)-oxy] methyl]butyl ester in 5 mL of tetrahydrofuran and the reaction mixture is stirred overnight. The reaction mixture is poured into water and extracted with three 50 mL portions of ether. The combined organic layers are dried over MgSO$_4$ and concentrated in vacuo affording crude product. Pure material is obtained by flash chromatography with 10% ethyl acetate/hexane as eluant affording 722 mg (54%) of (Z)-9-octadecenylcarbamic acid (E)-1-[[(3,7-dimethyl-2,6-octadienyl)oxy]methyl]-4-hydroxybutyl ester. Next, 2 mL of 2.0M Jones reagent is added at 0° C. to a solution of 722 mg (1.33 mmol) of (Z)-9-octadecenylcarbamic acid (E)-1-[[(3, 7-dimethyl-2,6-octadienyl)oxy]-methyl]-4-hydroxybutyl ester in 12 mL of acetone and the reaction is stirred for 3 hours. The reaction is poured into water and extracted with three 50 mL portions of ether. The combined organic layers are dried over MgSO$_4$ and concentrated in vacuo affording crude product. Pure material was obtained by flash chromatography with 35% ethyl acetate/hexane as eluant affording 226 mg (30%) of 5-[((E)-3,7-dimethyl-2,6-octadienyl)oxy] -4-[[((Z)-9-octadecenylamino) carbonyl]oxy]pentanoic acid.

Spectral data follows: $^1$H NMR (CDCl$_3$, 400 MHz) δ 5.336 (m, 3H, HC=CH), 5.076 (m, 1H, HC=C), 4.903 (m, 1H, HCOC=O), 4.751 (m, 1H, NH), 4.001 (m, 2H, OCH$_2$), 3.487 (d, 2H, OCH$_2$), 3.143 (d, 2H, O=CCH$_2$, HNCH$_2$), 2.422 (t, 2H, HO$_2$CCH$_2$), 2.076 (m, 8H, C=CCH$_2$), 1.666 (s, 3H, C=CCH$_3$), 1.640 (s, 3H, C=CCH$_3$), 1.588 (s, 3H, C=CCH$_3$), 1.466 (m, 4H, O=CCH$_2$CH$_2$, NHCH$_2$CH$_2$), 1.256 (m, 22H, CH$_2$), 0.869 (t, 3H, CH$_2$CH$_3$); IR (KBr) 3350, 2940, 2870, 1725, 1545, 1455, 1380, 1250, 1130 cm$^{-1}$; MS (CI$^+$) 564 (MH$^+$), 429, 428, 410, 153, 137 (100), 135, 117, 99, 81.

Analysis Calc'd. for C$_{34}$H$_{61}$NO$_5$: C, 72.42; H, 10.90; N, 2.48 Found: C, 72.13; H, 10.53; N, 2.41.

B) ((Z)-9-octadecynyl)carbamic acid 1-[[((E)-3,7-Dimethyl-2,6-octadecadienyl)-oxy]methyl]-4-(2,5-dihydro-4-hydroxy-2-oxo-3-furanyl)-4oxobutyl ester To a stirring solution of 146 mg (1.46 mmol) of tetronic acid in 10 mL of dimethylformamide is added 200 µL (1.46 mmol) of triethylamine and 75 mg of 4-dimethylaminopyridine at 0° C. Next, 300 mg (1.56 mmol) of 1-(3-dimethylaminopropyl)-3-ethylcarbodiimide hydrochloride and 810 mg( 1.46 mmol) of 5-[((E)-3,7-dimethyl-2,6-octadienyl)oxy]-4-[[((Z)-9-octadecenylamino)carbonyl]oxy]pentanoic acid are added and the reaction mixture is stirred for 2 days at room temperature. The reaction mixture is acidified with 1.0N HCl and extracted with three 50 mL portions of ether. The combined organic layers are dried over MgSO$_4$ and concentrated in vacuo affording crude product. Pure material was obtained by flash chromatography with 10% methanol/ethyl acetate as eluant affording 800 mg (86%) of ((Z)-9-octadecynyl)-carbamic acid 1-[[((E)-3,7-dimethyl-2,6-octadecadienyl)oxy]methyl]-4-(2,5-dihydro-4-hydroxy-2-oxo-3-furanyl)-4-oxobutyl ester.

Spectral data follows: $^1$H NMR (CDCl$_3$, 400 MHz) δ 5.351 (m, 3H, HC=CH), 5.090 (m, 1H, HC=C), 4.918 (m, 1H, HCOC=O), 4.747 (m, 1H, NH), 4.667 (s, 2H, CH$_2$O C=O), 4.039 (m, 2H, OCH$_2$), 3.515 (d, 2H, OCH$_2$), 3.136 (m, 2H, NHCH$_2$), 3.033 (m, 2H, O=CCH$_2$), 2.076 (m, 8H, C=CCH$_2$), 1.683 (s, 3H, C=CCH$_3$), 1.658 (s, 3H, C=CCH$_3$), 1.605 (s, 3H, C=CCH$_3$), 1.483 (m, 4H, O=CCH$_2$CH$_2$ $_{HNCH2}$CH$_2$), 1.256 (m, 22H, CH$_2$), 0.865 (t, 3H, CH$_2$CH$_3$); IR (film) 3360, 2930, 2860, 1775, 1725, 1705, 1605, 1525, 1460, 1440, 1375, 1245, 1125, 1040, 1015 cm$^{-1}$; MS (CI$^+$) 646 (MH$^+$), 511, 510, 492, 412, 411, 410 (100), 209, 199, 153, 137, 81.

Analysis Calc'd. for C$_{38}$H$_{63}$NO$_7$: C, 70.66; H, 9.83; N, 2.17 Found: C, 70.60; H, 9.48; N, 1.92.

EXAMPLE 15

4-Hydroxy-3-[(Z)-8-(2-octylcyclopropyl)-1-oxooctyl]-2-(5H)-thiophenone

To 2.2 g of zinc-copper couple in 30 mL of dry ether is added 5.7 mL (16.9 mmol) of methyl oleate and 5.4 mL (70.7 mmol) of diiedomethane. The reaction mixture is refluxed overnight, cooled to room temperature, poured into 1.0N HCl, and extracted three times with ether. The organic layers are combined, washed with brine, dried over MgSO$_4$, filtered, and concentrated in vacuo to give an oil. The oil is subjected to the conditions described in Example 51 above to give an oil free of starting material. The oil is taken up in a combination of tetrahydrofuran :methanol:water (2:1:1), followed by the addition of 4.0 g of 85% KOH. After 4 hours stirring at room temperature, the solvents are evaporated, the residue taken up in 0.1N KOH, and extracted three times with ether. The aqueous phase is acidified using concentrated HCl and extracted three times with ether. The ether layers are combined, washed with brine, dried over, MgSO$_4$, filtered, and concentrated in vacuo to give cis-8-(2-octylcyclopropyl) octanoic acid. Spectral data follows: $^1$H NMR (CDCl$_3$, 400 MHz) δ 2.35 (t, 2H, J=7.0 Hz, CH$_2$C=O), 0.6–1.7 (m, 33H).

To a stirring solution of 330 mg (2.84 mmol) of thiotetronic acid in 20 mL of dimethylformamide is added 410 µL (2.94 mmol) of triethylamine and 100 mg (820 µmmol) of 4-dimethylaminopyridine at 0° C. Next, 640 mg (3.33 mmol) of 1-(3-dimethylaminopropyl)-3-ethylcarbodiimide hydrochloride and 1.0 g (3.38 mmol) of cis-8-(2-octylcyclopropyl)octanoic acid are added and the reaction mixture is stirred overnight at room temperature. The reaction is acidified with 1.0N HCl and extracted three times with ethyl acetate. The combined organic layers are washed with brine, dried over MgSO$_4$, and concentrated in vacuo. The residue is recrystallized from 5% ethyl acetate/hexanes, filtering to give 250 mg (22%) of 4-hydroxy-3-[

(Z)-8-(2-octylcyclopropyl)-1-oxooctyl]-2(5H)-thiophenone, mp 30°-32° C.

Spectral data follows: $^1$H NMR (CDCl$_3$,400 MHz) δ 4.0 (s, 2H, CH$_2$SC=O), 2.96 (t, 2H, J=7.5 Hz, O=CCH$_2$), 1.65 (m, 2H, CH$_2$), 1.2–1.4 m, 12H, aliphatic), 0.88 (t, 2H, J=7 Hz, cyclopropyl), 0.60 (m, 2H, cyclopropyl); IR (KBr) 2910, 2840, 1685 (C=O), 1620, 1570 cm$^{-1}$; MS (EI) 394 (M+).

Analysis Calc'd. for C$_{22}$H$_{38}$SO$_3$: C, 70.01; H, 9.71 Found: C, 70.13; H, 9.52.

EXAMPLE 16

4-Hydroxy-3-[(Z)-1-oxo-2-(2-pentylcyclopropy) ethyl]-2(5H)-furanone

Cis-nonen-1-ol (10.0 g) is subjected to the cyclopropanation conditions as described in the preparation of Example 52. The resulting residue is taken up in 100 mL of dichloromethane at 0° C., followed by the addition of 800 mg of sodium bromide in 2 mL of water and 150 mg of 2,2,6,6-tetramethyl-1-piperidinyloxy, free radical. To this mixture is added 1.50 g of Aliquot 336 followed by the dropwise addition of 9.2 g of sodium bicarbonate in 230 mL of 5% NaOCl. The aqueous phase is made basic, separated from the organic phase and acidified with concentrated HCl, and then extracted three times with dichloromethane. The combined organic layers are washed with water, dried over MgSO$_4$, and concentrated in vacuo to give cis-2-(2'-pentylcyclopropyl) acetic acid.

Spectral data follows: $^1$H NMR (CDCl$_3$, 400 MHz) δ 1.5 (m, 2H, CH$_2$C=O), 0.8–1.6 (m, 15H, aliphatic).

To a stirring solution of 500 mg( 5.0 mmol) of tetronic acid in 20 mL of dimethylformamide is added 250 μL (1.79 mmol) of triethylamine and 220 mg (1.80 mmol) of 4-dimethylaminopyridine at 0° C. Next, 1.13 g (5.89 mmol) of 1-(3-dimethylaminopropyl)-3-ethylcarbodiimide hydrochloride and 1.0 g (5.89 mmol) of cis-2-(2'-pentylcyclopropyl)acetic acid are added and the reaction mixture is stirred overnight at room temperature. The reaction is acidified with 1.0N HCl and extracted three times with ethyl acetate. The combined organic layers are washed with brine, dried over MgSO$_4$, and concentrated in vacuo. The residue is recrystallized from pentane, filtering to give 80 mg (6%) of 4-hydroxy-3-[(Z)-1-oxo-2-(2-pentylcyclopropyl) ethyl]-2(5H)-furanone, mp 55°-58° C.

Spectral data follows: $^1$H NMR (CDCl$_3$,400 MHz) δ 4.67 (s, 2H, CH$_2$OC=O), 2.9 (m, 4H, CH$_2$cyclopropyl and O=CCH$_2$), 1.1–1.5 (m, 14H, aliphatic), 0.9 (m, 6H, CH$_3$ and cyclopropyl), 0.70 (m, 2H, cyclopropyl); IR (KBr) 2920, 2840, 1770 (C=O), 1650, 1610 cm$^{-1}$; MS (EI) 252 (M+).

Analysis Calc'd. for C$_{13}$H$_{20}$O$_4$: C, 66.65; H, 7.99 Found: C, 65.36; H, 7.27.

EXAMPLE 17

4-Hydroxy-3-3-[(Z)-8-(2-butylcyclopropyl)-1-oxooctyl]-2(5H)-furanone

Methyl myristoleate (1.5 g) is subjected to the cyclopropanation and saponification conditions described above for Example 52 to give cis-8-(2'-butylcyclopropyl) octanoic acid.

Spectral data follows: $^1$H NMR (CDCl$_3$, 400 MHz) δ 2.35 (t, 2H, J=7.5 Hz, CH$_2$C=O), 0.6–1.8 (m, 25H).

To a stirring solution of 300 mg (3.0 mmol) of tetronic acid in 20 mL of dimethylformamide is added 460 μL (3.21 mmol) of triethylamine and 700 mg (5.74 mmol) of 4-dimethylaminopyridine at 0° C. Next, 700 mg (3.65 mmol) of 1-(3-dimethylaminopropyl)-3-ethylcarbodiimide hydrochloride and 820 mg (3.42 mmol) of cis-8-(2'-butylcyclopropyl)octanoic acid are added and the reaction mixture is stirred overnight at room temperature. The reaction is acidified with 1.0N HCl and extracted three times with ethyl acetate. The combined organic layers are washed with brine, dried over MgSO$_4$, and concentrated in vacuo. The residue was subjected to flash chromatography (acid washed silica gel) eluting with 50% ethyl acetate/hexanes to give 10 mg(10%) of 4-hydroxy-3-[(Z)-8-(2-butylcyclopropyl)-1-oxooctyl]-2(5H)-furanone as a yellow wax.

Spectral data follows: $^1$H NMR (CDCl$_3$, 400 MHz) δ 4.68 (s, 2H, CH$_2$OC=O), 2.92 (t, 2H, J=7.5 Hz, O=CCH$_2$), 0.60–2.0 (m, 15H,cyclopropyl and aliphatic); IR (KBr) 2920, 2850, 1780 (C=O), 1750, 1650, 1610 cm$^{-1}$; MS (EI) 322 (M+).

Analysis Calc'd. for C$_{19}$H$_{30}$O$_4$: C, 70.77; H, 9.38 Found: C, 70.06; H, 8.86.

EXAMPLE 18

4-Hydroxy-3-[(Z)-1-oxo-5-(2-undecylcyclopropyl) pentyl]-2(5H)-furanone

Methyl petroselinate (2.5 g) was subjected to the cyclopropanation and saponification conditions described in Example 52 to give cis-5-(2'-undecylcyclopropyl) pentanoic acid.

Spectral data follows: $^1$H NMR (CDCl$_3$, 400 MHz) δ 5 2.35 (t, 2H, J=7 Hz, CH$_2$C=O), 0.6–1.8 (m, 33H, aliphatic).

To a stirring solution of 420 mg (4.20 mmol) of tetronic acid in 20 mL of dimethylformamide is added 640 μL (4.59 mmol) of triethylamine and 160 mg( 1.31 mmol) of 4-dimethylaminopyridine at 0° C. Next, 1.0 g (5.20 mmol) of 1-(3-dimethylaminopropyl)-3-ethylcarbodiimide hydrochloride and 1.5 g (5.06 mmol) of cis-5-(2'-undecylcyclopropyl) pentanoic acid are added and the reaction mixture is stirred overnight at room temperature. The reaction is acidified with 1.0N HCl and extracted three times with ethyl acetate. The combined organic layers are washed with brine, dried over MgSO$_4$, and concentrated in vacuo. The residue is subjected to flash chromatography (acid washed silica gel) eluting with 50% ethyl acetate/hexanes to give a 400 mg (25%) of 4-hydroxy-3-[(Z)-1-oxo-5-(2-undecylcyclopropyl)pentyl]-2(5H)-furanone as a yellow solid, mp 40°-42° C.

Spectral data follows: $^1$H NMR (CDCl$_3$,400 MHz) δ 4.68 (s, 2H, CH$_2$OC=O), 2.95 (t, 2H, J=7.5 Hz, O=CCH$_2$), 0.60–2.1 (m, 20H,cyclopropyl and aliphatic); IR (KBr) 2920, 2840, 1770 (C=O), 1690, 1600 cm$^{-1}$; MS (EI) 378 (M+).

Analysis Calc'd. for C$_{23}$H$_{38}$O$_4$: C, 72.98; H, 10.12 Found: C, 72.64; H, 8.88.

EXAMPLE 19

4-Hydroxy-3-[ (Z)-1-oxo-2(2-pentylcyclopropyl) ethyl]-2(5H)-thiophenone

Cis-nonen-1-ol (10.0 g) is subjected to the cyclopropanation conditions described in the preparation of Example 52. The resulting residue is taken up in 100 mL of dichloromethane at 0° C., followed by the addition of 800 mg of sodium bromide in 2 mL of water and 150 mg of 2,2,6,6- tetramethyl-1-piperidinyloxy, free radical. To this mixture is added 1.50 g of Aliquot 336 followed by the dropwise addition of 9.2 g of sodium bicarbonate in 230 mL of 5% NaOCl. The aqueous phase is made basic, separated from the organic phase and acidified with concentrated HCl, and then extracted three times with dichloromethane. The combined organic layers are washed with water, dried over $MgSO_4$, and concentrated in vacuo to give cis-2-(2'-pentylcyclopropyl) acetic acid.

Spectral data follows: $^1H$ NMR ($CDCl_3$, 400 MHz) δ 1.5 (m, 2H, $CH_2C=O$), 0.8–1.6 (m, 15H, aliphatic).

To a stirring solution of 2.0 g (17.2 mmol) of thiotetronic acid in 20 mL of dimethylformamide is added 2.6 mL (18.64 mmol) of triethylamine and 640 mg (5.25 mmol) of 4-dimethylaminopyridine at 0° C. Next, 4.0 g (20.8 mmol) of 1-(3-dimethylaminopropyl)-3-ethylcarbodiimide hydrochloride and 3.5 g (20.6 mmol) of cis-2-(2'-pentylcyclopropyl)acetic acid are added and the reaction mixture is stirred overnight at room temperature. The reaction is acidified with 1.0N HCl and extracted three times with ethyl acetate. The combined organic layers are washed with brine, dried over $MgSO_4$, and concentrated in vacuo. The residue is subjected to flash chromatography (acid washed silica gel) eluting with 10% ethyl acetate/hexanes to give 400 mg (9%) of 4-hydroxy-3-[(Z)-1-oxo-2-(2-pentylcyclopropyl)ethyl]-2(5H)-thiophenone as an orange oil.

Spectral data follows: $^1H$ NMR ($CDCl_3$, 400 MHz) δ 4.0 (s, 2H, $CH_2SC=O$), 3.0 (m, 4H, $CH_2$cyclopropyl and $O=CCH_2$), 1.65 (m, 2H, $CH_2$), 0.7–1.5 (m, 10H, aliphatic); IR (KBr) 2920, 1685 (C=O), 1620, 1570 $cm^{-1}$; MS (EI) 268 (M+).

Analysis Calc'd. for $C_{13}H_{20}SO_3$ : C, 62.66; H, 7.51 Found: C, 62.84; H, 7.36.

EXAMPLE 20

The compounds of the invention are tested in an in vitro phospholipase $A_2$ assay to determine the ability of the compounds to inhibit the biosynthesis of platelet-activating factor and $LTB_4$ in purified human neutrophils.

This Assay is carried out as follows:
Isolation of Human Poymorphonuclear Neutrophils:

A leukocyte enriched blood sample obtained from a healthy male donor is procured by leukophoresis using a Haemonetics model 30+ blood processor (Biological Specialties, Inc., Lansdale, Pa). The top "platelet-rich" layer is removed after a low speed spin (35×g, 15 min, 25° C.) of the sample. The remaining cell suspension is centrifuged (400×g, 10 min, 25° C.) to sediment the remaining cells. The supernatant is discarded and the cell pellet resuspended in 120 ml HBSS (without $Ca^{++}/Mg^+$). The cell suspension is subjected to ficoll-hypaque sedimentation (Histopaque 1077, 400×g, 30 min, 25° C.). Contaminating erythrocytes are lysed by hypotonic shock (1 min). The cells are then washed once with 40 ml of HBSS and resuspended with HBSS (without $Ca^{++}/Mg^{++}$) to a concentration of $2.5×10^7$ cells/ml for further use. Greater than 95% purity is obtained, as assessed by microscopic examination.

Platelet-Activating Factor Biosynthesis in Human Polymorphonuclear Neutrophils (PMN)

One ml of human PMN ($2.5×10^7$ cells/ml) is incubated with vehicle or drugs (10 μl) for 10 minutes at 30° C. After preincubation, an equal volume of HBSS (1 ml) containing 2.4 mM $CaCl_2$, 6 μM calcium ionophore A23187 and 50 μCi [$^3H$]-acetate is then incubated at 30° C. for 15 minutes. An aliquot (100 μl) of the reaction mixture is taken out and mixed with 900 μl of 15% ethanol. $LTB_4$ is extracted by using solid phase extraction on reverse phase $C_{18}$ columns to remove excess [$^3H$]-acetate and PAD. The $C_{18}$ column is prewashed once with 2 ml of ethanol and water. The sample aliquot is acidified with 0.1N HCl to pH 3 before applying to the column. The column is then washed with 2 ml of water followed by 2 ml of 15% ethanol and 2 ml of petroleum ether to remove excess labeled acetate. The sample is eluted with 2 ml of ethyl acetate. The collected samples are dried with nitrogen and resuspended in 0.5 ml RIA buffer. The quantity of $LTB_4$ in the sample is obtained from RIA determination. For PAF determination, the reaction is terminated by addition of 5 ml chloroform:methanol:acetic acid (2:1:0.04, v/v/v). [3H]-PAF is obtained by Bligh and Dyer extraction. The chloroform phase is removed and dried under nitrogen. The residue is redissolved in 75 μl of chloroform:methanol (80:20, v/v). [$^3H$]-PAF is resolved from other phospholipids by TLC on $RPCl_{18}$ plates with a solvent system of chloroform:methanol:water (2:3:1, v/v/v) and is quantitated using a Berthold automated TLC linear analyzer.

Data presented are the mean +/– s.d. of the values relative to control A23187 stimulated cells for each experiment assayed in triplicate. Percent inhibition when used is calculated as:

% Inhibition=100–[(x+Control)×100]

Dose response analysis is performed by non-linear regression analysis for curve fitting and $IC_{50}$ determination.

In this assay, scalaradial, an irreversible inhibitor of $PLA_2$, isolated from the marine sponge *Cacospongia sp.* gives an $IC_{50}$ of 1.0 μM.

When tested in this assay, the compounds of the invention gave the following results:

TABLE III

| Compound of Example No. | Dose, μM | % Inhibition PAF | Dose, μM | % Inhibition $LTB_4$ |
|---|---|---|---|---|
| 3 | 10 | 24 | 10 | 93 |
|   | 25 | 49 | 25 | 91 |
|   | 50 | 67 |   |   |

EXAMPLE 21

The compounds of the invention are tested in an in vitro isolated phospholipase $A_2$ assay to determine the ability of the test compounds to inhibit the release of arachidonic acid from an arachidonic acid-containing substrate by the action of phospholipase $A_2$ enzyme from human and non-human sources.

This assay is carried out as follows:

Into a 15 mL polypropylene tube are added the following:

| Agent | Volume, μL | Final Conc. |
|---|---|---|
| $^3H$-AA *E. coli* substrate[1] | 25 | 5 nmoles PL |
| $CaCl_2$ (0.1M)[2] | 5 | 5 mM |
| Tris-HCl (0.5M) pH 7.5[3] | 20 | 100 mM |
| Water[4] | 25 | |
| Drug/vehicle[5] | 1 | 50 μm |
| $PLA_2$ | 25 | Volume yielding 12% hydrolysis in 10 min. |
| | 100 | |

*pre-incubate at room temperature 30 min prior to substrate addition.

| Agent | Volume, μL | Final Conc. |
|---|---|---|

¹Prepared by adding 2 mL deionized and distilled water to 2 mL ³H-arachidonate labeled *E. coli* (lower count), to which is added 1 mL of ³H-arachidonate labeled *E. coli* (higher count) to yield a total of 5 m substrate (containing 1000 mmoles phospholipid).
²Stock 0.1 m $CaCl_2$, required for enzyme activity.
³Stock 0.5 m Trisma-Base.
Stock 0.5 M Trisma-HCl. Adjust pH to 7.5 (optimum for enzyme).
⁴Deionized and distilled water.
⁵Stock 10 mM prepared in dimethyl sulfoxide. Make 1:2 dilution with dimethyl sulfoxide and add 1 μL to 100 μL assay tube.
⁶Two human $PLA_2$ enzymes are used:
a) Semi-purified human platelet acid extract $PLA_2$ (in 10 mM sodium acetate buffer, pH 4.5). Remove protein precipitate by centrifugation at about 2200 rpm for 10 minutes.
b) Purified human synovial fluid.

Incubate the 100 μL reaction mixture for 10 minutes at 37° C. in a shaking water bath. The reaction is terminated by the addition of 2 mL tetrahydrofuran, followed by vortexing. $NH_2$ columns (100 μg/mL—Analytichem International) are conditioned with 0.5 mL tetrahydrofuran followed by 0.5 mL tetrahydrofuran/water (2 mL:0.1 mL, v/v).

The sample is loaded onto the columns and slowly drawn through them. The hydrolyzed arachidonic acid retained in the columns is eluted therefrom with 1 mL tetrahydrofuran/ glacial acetic acid (2%). The arachidonic acid is transferred to scintillation vials and quantitated by β-counting analysis. A "total counts" sample is prepared by pipetting 25 μL ³H-arachidonate *E. coli* directly into a scintillation vial to which is added 1 mL tetrahydrofuran. 10 mL aquasol (scintillation cocktail) is added to all samples.

Calculations:

$$\% \text{ hydrolysis} = \frac{[3H]AA \text{ dpm(sample)} - [3H]AA \text{ dpm(nonspecific hydrolysis)}}{\text{total counts dpm}} \times 100$$

$$\% \text{ change} = \frac{\text{vehicle dpm} - \text{drug dpm}}{\text{vehicle dpm}} \times 100$$

Activity of Standard Drugs:

| Drug | IC₅₀ (μM) | |
|---|---|---|
| | Human Platelet $PLA_2$ | Human Synovial $PLA_2$ |
| Arachidonic Acid | 8.6 | 3.2 |
| Monoalide | 25.2 | 0.14 |

When tested in this assay, the compounds of the invention gave the following results:

TABLE IV

| Compound of | % Inhibition at 10 μM | | IC₅₀ (μM) | |
|---|---|---|---|---|
| Example No. | HP* | HSF** | HP | HSF |
| sulindac | 33 | 34 | | 30.2 |
| 1 | 0 (at 50 μM) | 11 (at 50 μM) | | |
| 2 | 2.5 | 24 | | |
| 3 | 71 | 89.8 | 13.1 | 2.5 |
| 4A | 45.4 | 80.7 | | |
| 4 | 56.6 | 79.5 | | |
| 5 | 20.6 | 33.6 | | |
| 6 | 37.4 | 21.0 | | |
| 7A | 47.7 | 43.2 | | |
| 7 | 33.5 | 34.5 | | |
| 8 | 31.6 | 15.1 | | |
| 9 | 37.1 | +10.0 | | |
| 11 | 22.5 | +35.7 | | |

TABLE IV-continued

| Compound of | % Inhibition at 10 μM | | IC₅₀ (μM) | |
|---|---|---|---|---|
| Example No. | HP* | HSF** | HP | HSF |
| 12 | 80.9 | 18.8 | | |
| 13 | 24.4 | +20.3 | | |
| 14A | 87.7 | 74.2 | | |
| 14 | 96.5 | 91.0 | | |
| 15 | 8.4 | 18.6 | | |
| 16 | 1.7 | 0.1 | | |

*human platelet
**human synovial fluid

EXAMPLE 22

The ability of the compounds of the invention to act as inhibitors of the enzymes 5-lipoxygenase and cyclooxygenase is measured in the resident murine peritoneal macrophage assay.

This assay is carried out as follows:

Resident peritoneal macrophages are collected from female Swiss Webster mice (49 days old, 20–25 gms, Buckshire) by lavaging with 7–8 ml Hanks Balanced Salt Solution (HBSS) without $Ca^{++}$ and $Mg^{++}$ (GIBCO). The lavage fluid from several mice is pooled and centrifuged at 4° C. for 10 minutes at 400×g. The cell pellet is resuspended in Medium 199 (GIBCO) with HEPES buffer containing 100 μg/ml gentamicin. Two ml of the cell suspension (4×10⁶ cells) are then plated on 35 mm culture dishes (Nunc).

A macrophage monolayer is established after a 1–1.5 hour incubation of the cells at 37° C. in an atmosphere of 95% $O_2$ and 5% $CO_2$. The monolayers are washed 2× with 2 ml HBDSS, containing $Ca^{++}$ and $Mg^{++}$ after which 2 ml Medium 199 supplemented with 10% freshly thawed heat-inactivated fetal bovine serum and 100 μg/ml gentamicin is added for an overnight incubation.

Residual serum and cellular debris are removed from the monolayers by washing 3× with 2 ml HBSS containing $Ca^{++}$ and $Mg^{++}$. Macrophages are preincubated for 5 minutes with 1 ml serum-free M199 containing 10 μl dimethyl sulfoxide (DMSO) vehicle or test compound prior to cell activation with zymosan (100 Mg/ml) or arachidonic acid (AA) (2 μM). After 2 hours, the supernatants are removed and either assayed for $LTC_4$ and $PGE_2$ by radioimmunoassay (RIA) directly or stored at −20° C. In all cases, results are expressed as ng metabolite/4×10⁶ cells.

Summary of RIAs used for quantitation of metabolite levels in zymosan or arachidonic acid stimulated mouse macrophage culture media.

| Metabolite | Range of detection (μg/ml) | Metabolite Levels (ng/4 × 10⁶ cells) (x ± S.E.M., n) |
|---|---|---|
| $LTC_4$ | 0.25–16 | 93.7 ± 9.9 (34) |
| $PGE_2$ | 0.027–20 | 30.90 ± 1.93 (39) |

Calculations:

Raw data (dpm) may be stored directly onto an "Autostart" tape using the HP85 in room C-096. The raw data are converted to ng metabolite/4–10⁶ cells using the standard curve by a "RIANAL" program (HP85) or a "NONLIN" program (HP9816). Results are then expressed as percent inhibition of zymosan induced, leukotriene or prostaglandin synthesis (control) using the equation:

$$\% \text{ Inhibition} = \frac{\text{control metabolite level} - \text{sample metabolite level}}{\text{control metabolite level}} \times 100$$

REFERENCE COMPOUNDS:

The compounds used are listed below.

$IC_{50}$ values of reference 5-lipoxygenase and/or cyclooxygenase inhibitors.

| Compound | $IC_{50}$ μM (95%) Confidence limits | |
|---|---|---|
| | $LTC_4$ | $PGE_2$ |
| BW 755c | 0.21 | 1.04 |
| | (0.10, 0.42) | (0.73, 1.49) |
| ETYA | 0.44 | 1.26 |
| | (0.36, 0.53) | (0.99, 1.60) |
| Indomethacin | >50 | 0.002 |
| | | (0.001, 0.003) |
| NDGA | 1.87 | 2.15 |
| | (0.22, 15.57) | (1.15, 4.04) |

When tested in this assay, the compounds of the invention exhibited the following levels of enzyme inhibition:

analysis of variance with Dunnett's comparisons to control (P=0.05). Drug effects are expressed as a percent change from control values:

$$\% \text{ change from control} = \frac{(\text{Rt. ear} - \text{Lt. ear})\text{drug} - (\text{Rt. ear} - \text{Lt. ear})\text{control}}{(\text{Rt. ear} - \text{Lt. ear})\text{control}} \times 100$$

Activity of standard drugs:

| Drug | Oral $ED_{50}$ (mg/kg) | |
|---|---|---|
| | (AA) | (TPA) |
| BW755c | 65 | 88 |
| Phenidone | 85 | 235 |
| Indomethacin | inactive at 10 | inactive at 10 |

The results for compounds of the invention tested in this assay are presented in table VIII.

TABLE V

| Compound of Example No. | $PGE_2$ | | | | $LTC_4$ | | | |
|---|---|---|---|---|---|---|---|---|
| | zymosan | | AA | | zymosan | | AA | |
| | Dose μM | % Inhibition | $IC_{50}$ | Dose μM | % Inhibition | Dose μM | % Inhibition | $IC_{50}$ | Dose μM | % Inhibition |
| 3 | | | 0.2 | | | | | 0.2 | | |
| 6 | 1.0 | 45.8 | | | | 1.0 | 41.5 | | | |
| 12 | 1.0 | 75.8 | | | | 1.0 | 46.4 | | | |
| 14 | | 37 | 0.8 | | | | 87 | 0.8 | | |
| 17 | 0.1 | 49.5 | | | | 0.1 | 59.3 | | | |
| 18 | 0.1 | 39.2 | | | | 0.1 | 80.3 | | | |
| | 0.5 | 74.3 | | | | 0.5 | 64.2 | | | |

EXAMPLE 23

The ability of the compounds of the invention to inhibit inflammatory responses is examined in the in vivo arachidonic acid (AA)/12-o-tetradecanoylphorbol acetate (TPA)-induced murine ear edema assay.

This assay is carried out as follows:

Swiss Webster female mice (Buckshire), approximately 8 weeks old are placed into plastic boxes in groups of six. Eight groups of mice receive AA topically on the right ear, and another 8 groups receive TPA topically on the right ear. AA and TPA are dissolved in acetone at concentrations of 100 mg/ml and 100 μg/ml respectively. The phlogistics are applied to the right ear by the means of an automatic pipet. Volumes of 10 μl are applied to the inner and outer surfaces of the ear. Each mouse receives either 2 mg/ear AA or 2 μg/ear TPA. The left ear (control) receives acetone delivered in the same manner. Topical and subcutaneous dosing regimens are as follows 1) drugs are given 30 minutes prior to AA treatment and 2) drugs are given 30 minutes after treatment with TPA.

Measurements are taken with Oditest calipers, 0–10 mm with 0.01 graduations. The right and left ears are measured after 1 hr AA-induced inflammation and 4 hours after TPA-induced inflammation.

Calculations:

The difference between right and left ear thickness is calculated and the significance is determined by a one way

TABLE VIII

| Compound of Example No. | TPA - Route of Drug Administration | | | | |
|---|---|---|---|---|---|
| | Topical | | | Subcutaneous | |
| | vehicle | % Inhibition at 200 μg | $IC_{50}$ | % Inhibition at 50 m/kg | $ED_{50}$ mg/kg |
| 3 | acetone | 40 | 450 | 36 | |
| 12 | acetone | 23 | | | |
| | acetone | 45 | | | |

What is claimed is:

1. A compound having the formula wherein

X is —$CH_2R$;

R is —$(CH_2)_bR^3$,

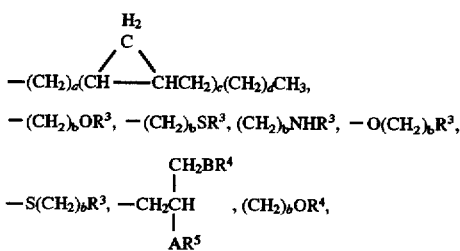

—$(CH_2)_d(CH$————$CHCH_2)_c(CH_2)_dCH_3$,

—$(CH_2)_bOR^3$, —$(CH_2)_bSR^3$, $(CH_2)_bNHR^3$, —$O(CH_2)_bR^3$,

—$S(CH_2)_bR^3$, 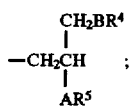 , $(CH_2)_bOR^4$, further when Y=S, R may also be —$(CH_2)_eCH_3$;

Y is —O— or —S—;

$R^1$ and $R^2$ are each, independently, hydrogen or lower alkyl;

$R^3$ is indolyl, furyl, phenyl or phenyl optionally mono- or disubstituted independently by alkyl of 1–7 carbon atoms, —$C(CH_3)_2CH_2C(CH_3)_3$, haloloweralkyl, perfluoroalkyl, lower alkoxy, aryl alkoxy, halo or nitro; with the proviso that, when R is —$(CH_2)_bR^3$, $R^3$ is not furyl;

$R^4$ and $R^5$ are, independently, —$COCH_2R^7$, —$CO_2R^7$, —$CONHR^7$, geranyl or $CH_2R^3$;

$R^6$ is hydrogen or lower alkyl;

$R^7$ is geranyl and any moiety selected from R other than

—$CH_2CH$ 
      |
      $CH_2BR^4$
      |
      $AR^5$
;

A and B are, independently, —O—, —S— or —$NR^6$—; and a is 0–8;

b is 4–10;

c is 1–3;

d is 0–9; and e is 3–18;

or a pharmaceutically acceptable salt thereof.

2. A compound of claim 1 having the name 4-hydroxy-3-[6-(4-chlorophenoxy)-1-oxohexyl]-2(5H)-furanone or a pharmaceutically acceptable salt thereof.

3. A compound of claim 1 having the name 4-hydroxy-3-[1-oxo-8-[2-[(2-pentylcyclopropyl)methyl]cyclopropyl]octyl]-2(5H)-furanone or a pharmaceutically acceptable salt thereof.

4. A compound of claim 1 having the name (Z)-9-octadecanoic acid 5-(2,5-dihydro-4-hydroxy-3-furanyl)-5-oxo-1,2-pentanediyl ester or a pharmaceutically acceptable salt thereof.

5. A compound of claim 1 having the name 3-[9-(4-chlorophenoxy)-1-oxononyl]-4-hydroxy-2(5H)-furanone or a pharmaceutically acceptable salt thereof.

6. A compound of claim 1 having the name hexylcarbamic acid 5-(2,5-dihydro-4-hydroxy-2-oxo-3-furanyl)-5-oxo-1,2-pentanediyl ester or a pharmaceutically acceptable salt thereof.

7. A compound of claim 1 having the name dodecylcarbamic acid 5-(2,5-dihydro-4-hydroxy-2-oxo-3-furanyl)-5-oxo-1,2-pentanediyl ester or a pharmaceutically acceptable salt thereof.

8. A compound of claim 1 having the name 4-hydroxy-3-[6-[4-[(4-chlorophenyl)methoxyphenoxy]]-1-oxohexyl]-2(5H)-furanone or a pharmaceutically acceptable salt thereof.

9. A compound of claim 1 having the name 4-hydroxy-3-[6-[4-(hexyloxy)phenoxy]-1-oxohexyl]-2(5H)-furanone or a pharmaceutically acceptable salt thereof.

10. A compound of claim 1 having the name 4-hydroxy-3-[7-(4-chlorophenoxy)-1-oxoheptyl]-2(5H)-furanone or a pharmaceutically acceptable salt thereof.

11. A compound of claim 1 having the name 3-[6-(4-heptylphenoxy)-1-oxohexyl]-4-hydroxy-2(5H)-furanone or a pharmaceutically acceptable salt thereof.

12. A compound of claim 1 having the name (Z)-9-octadecanoic acid 4-(2,5-dihydro-4-hydroxy-2-oxo-3-furanyl)-4-oxobutanoic ester or a pharmaceutically acceptable salt thereof.

13. A compound of claim 1 having the name 4-hydroxy-3-[6-(1,1,3,3-tetramethylbutyl) phenoxy)-1-oxohexyl]-2(5H)-furanone or a pharmaceutically acceptable salt thereof.

14. A compound of claim 1 having the name ((Z)-9-octadecynyl)carbamic acid 1-[[((E)-3,7-dimethyl-2,6-octadecadienyl)oxy]methyl]-4-(2,5-dihydro-4-hydroxy-2-oxo-3-furanyl)-4-oxobutyl ester or a pharmaceutically acceptable salt thereof.

15. A compound of claim 1 having the name 4-hydroxy-3-[(Z)-8-(2-octylcyclopropyl)-1-oxooctyl]-2(5H)-thiophenone or a pharmaceutically acceptable salt thereof.

16. A compound of claim 1 having the name 4-hydroxy-3-[(Z)-1-oxo-2-(2-pentylcyclopropy)ethyl]-2(5H)-furanone or a pharmaceutically acceptable salt thereof.

17. A compound of claim 1 having the name 4-hydroxy-3-[(Z)-8-(2-butylcyclopropyl)-1-oxooctyl]-2(5H)-furanone.

18. A compound of claim 1 having the name 4-hydroxy-3-[(Z)-1-oxo-5-(2-undecylcyclopropyl)pentyl]-2(5H)-furanone or a pharmaceutically acceptable salt thereof.

19. A compound of claim 1 having the name 4-hydroxy-3-[(Z)-1-oxo-2-(2-pentylcyclopropyl)ethyl]-2(5H)-thiophenone or a pharmaceutically acceptable salt thereof.

* * * * *